(12) United States Patent
Hsu et al.

(10) Patent No.: US 11,730,915 B2
(45) Date of Patent: Aug. 22, 2023

(54) IMAGE DISPLAY METHOD AND IMAGE DISPLAY SYSTEM FOR ALLEVIATING MOTION SICKNESS

(71) Applicant: INDUSTRIAL TECHNOLOGY RESEARCH INSTITUTE, Hsinchu (TW)

(72) Inventors: Wei-Lin Hsu, Taichung (TW); Hong-Ming Dai, Tainan (TW)

(73) Assignee: INDUSTRIAL TECHNOLOGY RESEARCH INSTITUTE, Hsinchu (TW)

(*) Notice: Subject to any disclaimer, the term of this patent is extended or adjusted under 35 U.S.C. 154(b) by 0 days.

(21) Appl. No.: 17/529,718

(22) Filed: Nov. 18, 2021

(65) Prior Publication Data
US 2022/0160993 A1    May 26, 2022

Related U.S. Application Data

(60) Provisional application No. 63/116,166, filed on Nov. 20, 2020.

(30) Foreign Application Priority Data

Oct. 18, 2021    (TW) .................................. 110138578

(51) Int. Cl.
*B60R 16/037*    (2006.01)
*G09G 3/20*    (2006.01)
(Continued)

(52) U.S. Cl.
CPC .............. *A61M 21/00* (2013.01); *B60K 35/00* (2013.01); *B60R 16/037* (2013.01);
(Continued)

(58) Field of Classification Search
CPC ............ A61M 21/00; A61M 2021/005; A61M 2205/332; A61M 2205/3365;
(Continued)

(56) References Cited

U.S. PATENT DOCUMENTS 6,932,090 B1    8/2005    Reschke et al.
7,717,841 B2    5/2010    Brendley et al.
(Continued)

FOREIGN PATENT DOCUMENTS

TW    201314629 A  *   4/2013
TW    201314629 A1     4/2013
(Continued)

OTHER PUBLICATIONS

Taiwanese Office Action and Search Report for Taiwanese Application No. 110138578, dated Jul. 14, 2022.
(Continued)

*Primary Examiner* — Brent D Castiaux
(74) *Attorney, Agent, or Firm* — Birch, Stewart, Kolasch & Birch, LLP

(57) ABSTRACT

The present disclosure provides an image display method and an image display system for alleviating motion sickness. The image display method includes: obtaining a number of shock and speed information of a transportation; comparing at least one of the shock and speed information with one or more than one corresponding threshold to determine whether motion sickness occurs; and in response to the determination that motion sickness occurs, positioning a position of a first image displayed on a display unit according to the shock and speed information.

12 Claims, 4 Drawing Sheets

(51) Int. Cl.
*B60K 35/00* (2006.01)
*A61M 21/00* (2006.01)

(52) U.S. Cl.
CPC ..... *G09G 3/2096* (2013.01); *A61M 2021/005* (2013.01); *A61M 2205/332* (2013.01); *A61M 2205/3365* (2013.01); *B60K 2370/1529* (2019.05); *B60K 2370/167* (2019.05); *G09G 2320/0261* (2013.01)

(58) Field of Classification Search
CPC ...... A61M 2205/502; A61M 2205/505; A61M 2205/507; A61M 2205/609; A61M 2209/02; A61M 2209/088; A61M 2230/04; A61M 2230/06; A61M 2230/62; A61M 2230/63; B60K 35/00; B60K 2370/1529; B60K 2370/167; B60R 16/037; G09G 3/2096; G09G 3/20; G09G 2320/0261; G09G 2340/0464
See application file for complete search history.

(56) References Cited

U.S. PATENT DOCUMENTS

| | | | |
|---|---|---|---|
| 8,690,750 | B2 | 4/2014 | Krueger |
| 10,849,496 | B2 | 12/2020 | Murakami et al. |
| 10,997,946 | B2 | 5/2021 | Selan et al. |
| 2014/0176296 | A1 | 6/2014 | Morgan |
| 2019/0133511 | A1* | 5/2019 | Migneco .............. A61B 5/0077 |

FOREIGN PATENT DOCUMENTS

| | | |
|---|---|---|
| TW | 201814441 A | 4/2018 |
| TW | 201926018 A | 7/2019 |

OTHER PUBLICATIONS

Chen et al., "Visually Induced Motion Sickness: Effects of Translational Visual Motion Along Different Axes," Contemporary Ergonomics and Human Factors, May 2011, 8 pages total.

* cited by examiner

IMAGE DISPLAY METHOD AND IMAGE DISPLAY SYSTEM FOR ALLEVIATING MOTION SICKNESS

This application claims the benefit of U.S. Provisional application Ser. No. 63/116,166 filed Nov. 20, 2020, and Taiwan application Serial No. 110138578, filed Oct. 18, 2021, the disclosure of which are incorporated by reference herein in its entirety.

TECHNICAL FIELD

The disclosure relates in general to an image display method and an image display system for alleviating motion sickness.

BACKGROUND

Motion sickness is a balance disorder and occurs due to the difference between the motion perceived by the eyes and the motion perceived through the vestibule of the inner ears. When motion sickness occurs, in a mild case, one will present symptoms of nausea, dizziness, or poor appetite; in a severe case, one will present symptoms of vomiting or even syncope. Motion sickness may easily be triggered when one is reading at a transportation. Particularly, when modern people are at a transportation, they tend to read using various electronic devices, such as mobile phones, PC tablets or car monitors, not only affecting the vision but also tending to trigger motion sickness.

SUMMARY

According to one embodiment, an image display method for alleviating motion sickness. The image display method includes: obtaining a number of shock and speed information of a transportation; comparing at least one of the shock and speed information with one or more than one corresponding threshold to determine whether motion sickness occurs; in response to the determination that motion sickness occurs, positioning a position of a first image displayed on a display unit according to the shock and speed information.

According to another embodiment, an image display system. The image display system includes one or more than one detection unit, a display unit and a processing unit. The processing unit is coupled to the detection unit and the display unit. The processing unit is configured to: obtain a plurality of shock and speed information of a transportation using the one or more than one detection unit; compare the at least one of the shock and speed information with one or more than one corresponding threshold to determine whether motion sickness occurs; and in response to the determination that motion sickness occurs, position a position of a first image displayed on the display unit according to the shock and speed information.

The above and other aspects of the disclosure will become better understood with regard to the following detailed description of the embodiment (s). The following description is made with reference to the accompanying drawings.

Figure 1:
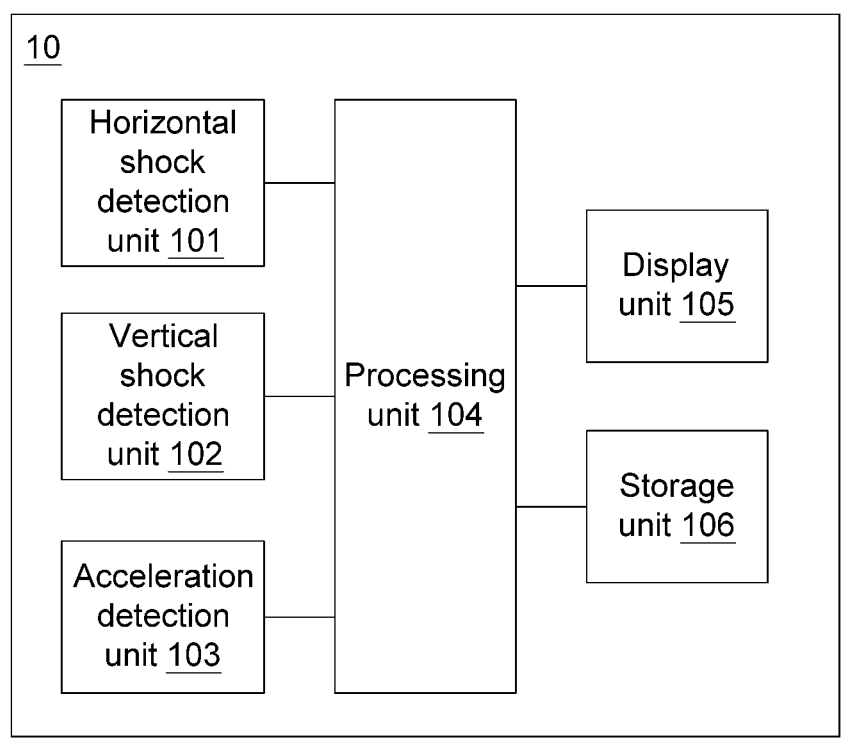
FIG. 1 is a block diagram of a display system according to an embodiment of the present disclosure.

In the following detailed description, for purposes of explanation, numerous details are set forth in order to provide a thorough understanding of the disclosed embodiments. It will be apparent, however, that one or more embodiments may be practiced without these details. In other instances, well-known structures and devices are schematically shown in order to simplify the drawing.

DETAILED DESCRIPTION

Figure 2:
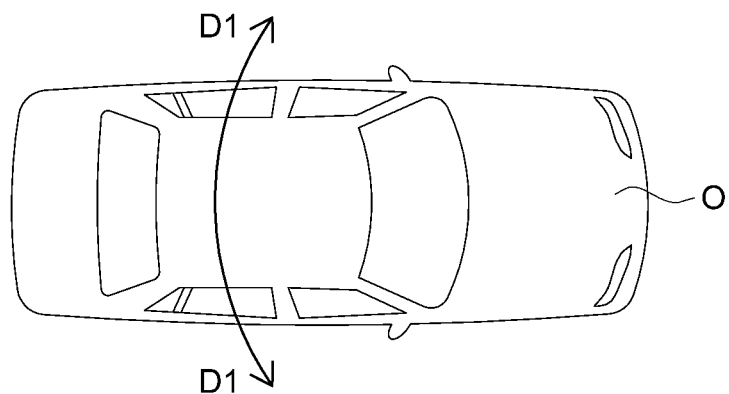
FIG. 2 is a schematic diagram of a horizontal direction.
Figure 3:
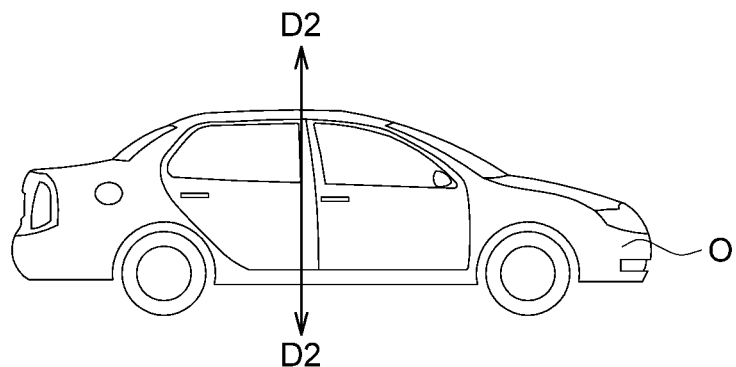
FIG. 3 is a schematic diagram of a vertical direction.
Figure 4:
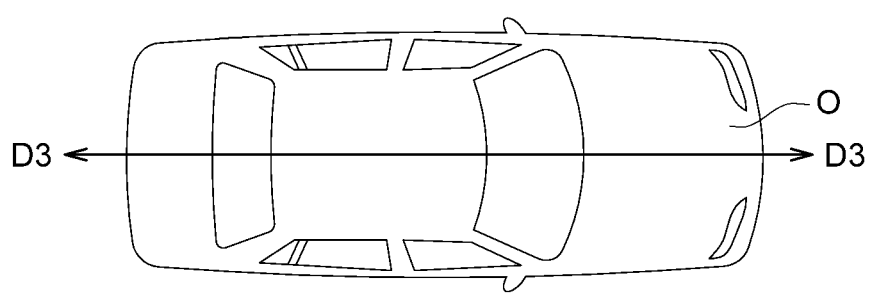
FIG. 4 is a schematic diagram of a moving direction.

Referring to FIG. 1, a block diagram of a display system according to an embodiment of the present disclosure is shown. The display system 10 includes a horizontal shock detection unit 101, a vertical shock detection unit 102, an acceleration detection unit 103, a processing unit 104, a display unit 105 and a storage unit 106. The horizontal shock detection unit 101 is configured to detect the amplitude and frequency of the shock in a direction parallel to a plane on which the transportation O is located, wherein the direction as indicated in FIG. 2 is referred as horizontal direction D1 hereinafter and the plane can be such as the ground, the sea level or any plane. The vertical shock detection unit 102 is configured to detect the amplitude and frequency of the shock in a direction vertical to a plane on which the transportation O is located, wherein the direction as indicated in FIG. 3 is referred as vertical direction D2 hereinafter. The acceleration detection unit 103 is configured to detect the acceleration of the transportation O in a moving direction D3 as indicated in FIG. 4. It should be noted that the moving direction D3 does not have to be perpendicular to the horizontal direction D1. The processing unit 104 is coupled to the horizontal shock detection unit 101, the vertical shock detection unit 102 and the acceleration detection unit 103 to receive the information detected by the horizontal shock detection unit 101, the vertical shock detection unit 102 and the acceleration detection unit 103. The display unit 105 is coupled to the processing unit 104. The storage unit 106 is coupled to the processing unit 104 to store a number of computer readable instructions. When the computer readable instructions are executed by the processing unit 104, the processing unit 104 is enabled to perform the image display method of the present disclosure. That is, the processing unit 104 determines whether motion sickness occurs according to the information detected by the horizontal shock detection unit 101, the vertical shock detection unit 102 and the acceleration detection unit 103. If the determination is positive, a position of a first image displayed on the display unit 105 is positioned according to the shock and speed information detected by the horizontal shock detection unit 101, the vertical shock detection unit 102 and the acceleration detection unit 103.

In an embodiment, the processing unit and the storage unit can be integrated to the transportation computer; the display unit, the horizontal shock detection unit, the vertical shock detection unit and the acceleration detection unit can be disposed on the transportation. In another embodiment, the display unit, the processing unit and the storage unit can be disposed on a mobile device; the horizontal shock detection unit and the vertical shock detection unit can be realized by G-sensors of the mobile device and can be connected to the transportation computer to obtain the information detected by the acceleration detection unit of the transportation. As disclosed above, the display unit, the processing unit, the storage unit, the horizontal shock detection unit, the vertical shock detection unit and the acceleration detection unit do not have to be integrated to the same electronic device or to the transportation. Besides, the horizontal shock detection unit and the vertical shock unit can be integrated to the same shock detection unit. For the present disclosure to be better understood, the unit which detects the amplitude and frequency of the shock in a horizontal direction is referred as horizontal shock detection unit, the unit which detects the amplitude and frequency of the shock in a vertical direction is referred as vertical shock detection unit, and the horizontal shock detection unit and the vertical shock detection unit do not have to be two independent elements or circuits.

Detailed descriptions of the image display method are disclosed below.

Firstly, through the reading comfort experiment, the horizontal shock amplitude threshold, the horizontal shock frequency threshold, the vertical shock amplitude threshold, the vertical shock frequency threshold and/or the acceleration threshold can be determined.

In an embodiment, the process of the reading comfort experiment is as follows. Firstly, experiment equipment and several testees are provided. The experiment equipment includes a display device, a transportation simulation device and one or more than one measurement device. The display device is configured to display images for the testees to view. The transportation simulation device is configured to simulate the speed and acceleration of the transportation as well as the amplitude and frequency of the horizontal and/or vertical shock. The measurement device is configured to measure a testee's heartbeat, heartbeat acceleration and/or balance parameter. The balance parameter can be measured through the gravity pedals of the two feet. Generally speaking, when a testee is in a balanced state, the force applied by the two feet is balanced; when a testee is dizzy or in a state of imbalance, the force applied by the two feet will change. The gravity pedals of the two feet can be used to measure the change in the force applied by the testee's two feet, and whether a testee is dizzy or in a state of imbalance can be determined according to the measured change in the force applied by the testee's two feet. After the testees' basic information, such as height, weight, age and gender, are obtained, the testees can be divided into several categories according to the basic information and an individual file is created for each testee. The measurement device can be used to measure each testee's heartbeat, heartbeat acceleration and/or balance parameter in a normal state (that is, the trustee has no motion sickness). The transportation simulation device is used to adjust several testing scenarios defined by the speed, the acceleration, the amplitude and frequency of the horizontal and/or vertical shock. Let each testee view the images displayed on a display device under different testing scenarios and let the measurement device be used to measure the testee's heartbeat, heartbeat acceleration and/or balance parameter to determine whether the testee has motion sickness. Based on the test results of all testees, the horizontal shock amplitude threshold, the horizontal shock frequency threshold, the vertical shock amplitude threshold, the vertical shock frequency threshold and/or the acceleration threshold beyond which all testees may present motion sickness can be generalized. Based on the test results of the testees of each category, the horizontal shock amplitude threshold, the horizontal shock frequency threshold, the vertical shock amplitude threshold, the vertical shock frequency threshold and/or the acceleration threshold beyond which the testees of each category may present motion sickness can be generalized. By comparing the horizontal shock amplitude threshold, the horizontal shock frequency threshold, the vertical shock amplitude threshold, the vertical shock frequency threshold and/or the acceleration threshold beyond which the testees of each category may present motion sickness with the horizontal shock amplitude threshold, the horizontal shock frequency threshold, the vertical shock amplitude threshold, the vertical shock frequency threshold and/or the acceleration threshold beyond which all testees may present motion sickness, the horizontal and/or vertical variable parameter corresponding to each category can be generalized. The horizontal variable parameter reflects the difference between the thresholds beyond which the testees of each category in the horizontal direction may present motion sickness and the thresholds beyond which all testees may present motion sickness. The vertical variable parameter reflects the difference between the threshold beyonds which the testees of each category in the vertical direction may present motion sickness and the thresholds beyond which all testees may present motion sickness.

For example, the testees include 100 males and 100 females. The female testees are allocated to the female category, and the male testees are allocated to the male category. Based on the experiment results of the 200 testees, various thresholds beyond which all testees may present motion sickness can be generalized. Based on the experiment results of the 100 male testees, various thresholds beyond which the testees of the male category may present motion sickness can be generalized. Based on the experiment results of the 100 male testees, various thresholds beyond which the testees of the female category may present motion sickness can be generalized. By comparing the various thresholds beyond which the testees of the male category may present motion sickness with the various thresholds beyond which all testees may present motion sickness, the horizontal and/or vertical variable parameter corresponding to the testees of the male category can be obtained. By comparing the various thresholds beyond which the testees of the female category may present motion sickness with the various thresholds beyond which all testees may present motion sickness, the horizontal and/or vertical variable parameter corresponding to the testees of the female category can be obtained.

The experiment results of the reading comfort experiment according to an embodiment of the present disclosure show that, for most testees, the horizontal shock is more likely to cause motion sickness than the vertical shock, and most testees are more sensitive to frequency than to amplitude. The reading comfort experiment of the present embodiment determines that the horizontal shock frequency threshold is 0.1 Hz, the horizontal shock amplitude threshold is 2 $m/s^2$, the vertical shock frequency threshold is 1 Hz, the vertical shock amplitude threshold is 5 cm, and the acceleration threshold is 9 $m/s^2$ and −9 $m/s^2$. It should be noted that the horizontal shock frequency threshold, the horizontal shock amplitude threshold, the vertical shock frequency threshold, the vertical shock amplitude threshold and the acceleration threshold hereinafter refer to the horizontal shock frequency threshold, the horizontal shock amplitude threshold, the vertical shock frequency threshold, the vertical shock amplitude threshold and the acceleration threshold that are determined according to the experiment results of all testees.

Figure 5:
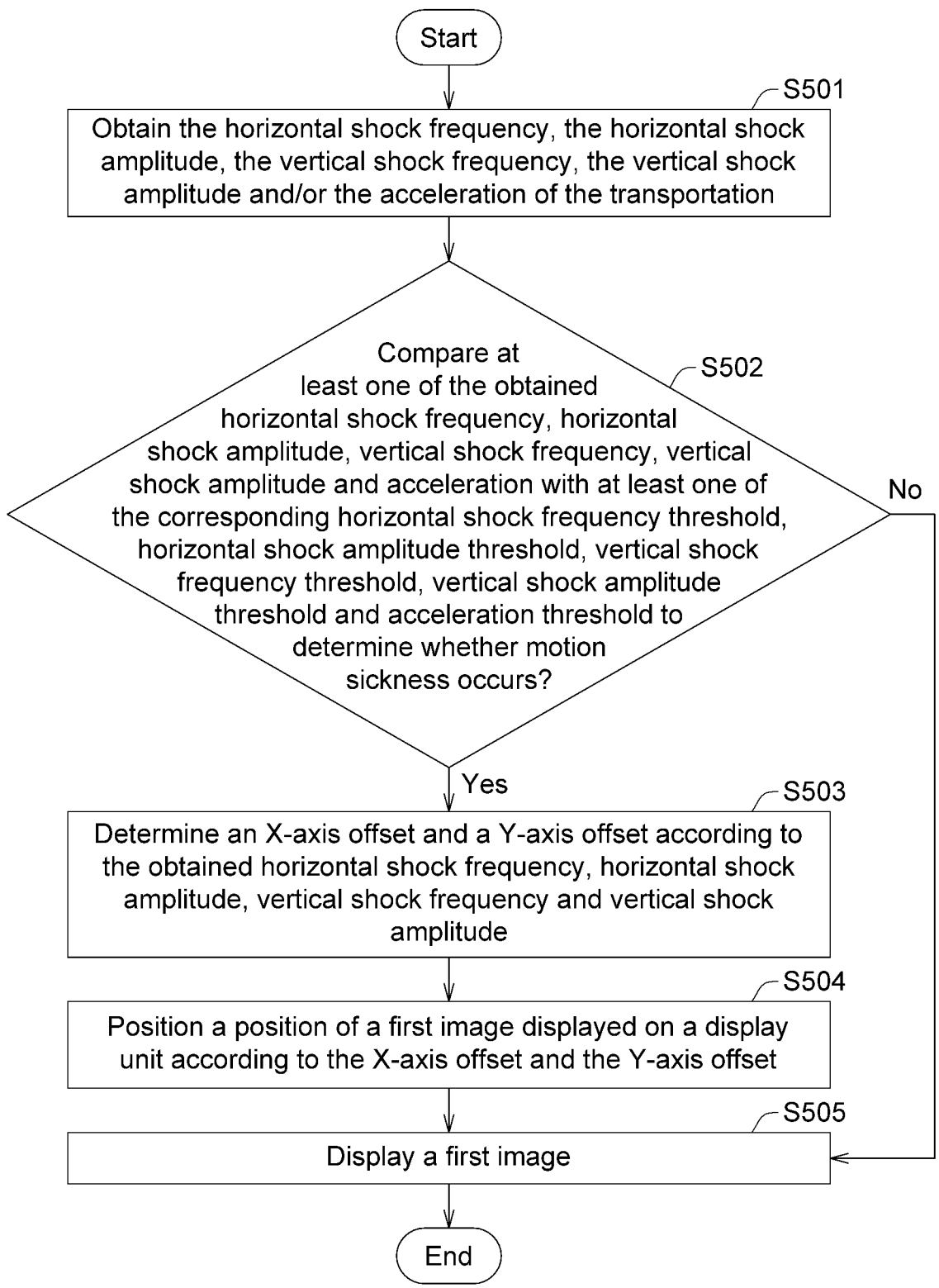
FIG. 5 is a flowchart of an image display method according to an embodiment of the present disclosure.

Referring to FIG. 5, a flowchart of an image display method according to an embodiment of the present disclosure is shown.

In step S501, the horizontal shock frequency, the horizontal shock amplitude, the vertical shock frequency, the vertical shock amplitude and/or the acceleration of the transportation are obtained. The horizontal shock frequency and the horizontal shock amplitude can be obtained using a horizontal shock detection unit. The vertical shock frequency and the vertical shock amplitude can be obtained using a vertical shock detection unit. The acceleration can be obtained using an acceleration detection unit.

In step S502, at least one of the obtained horizontal shock frequency horizontal shock amplitude, vertical shock frequency, vertical shock amplitude and acceleration is compared with at least one of the corresponding horizontal shock frequency threshold, horizontal shock amplitude threshold, vertical shock frequency threshold, vertical shock amplitude threshold and acceleration threshold to determine whether motion sickness occurs. If the determination is positive, then the method proceeds to step S503; if the determination is negative, then the method proceeds to step S505.

In an embodiment, whether motion sickness occurs can be determined according to the horizontal shock frequency, the vertical shock frequency and the acceleration. In the present embodiment, it can be determined that motion sickness when at least one of the horizontal shock, the vertical shock frequency and the acceleration meets the corresponding horizontal shock frequency threshold, vertical shock frequency threshold or acceleration threshold. For example, given that the horizontal shock frequency threshold is 0.1 Hz, the vertical shock frequency threshold is 1 Hz, and the acceleration threshold is 9 m/s$^2$ and −9 m/s$^2$, it can be determined that motion sickness will occur as long as at least one of the three conditions is met. The three conditions are: the horizontal shock frequency is not smaller than 0.1 Hz, the vertical shock frequency is not smaller than 1 Hz, and the acceleration is not smaller than 9 m/s$^2$ and not greater than −9 m/s$^2$.

In step S503, an X-axis offset and a Y-axis offset are determined according to the obtained horizontal shock frequency, horizontal shock amplitude, vertical shock frequency and vertical shock amplitude. The X-axis offset=$n_x * A_{1x} * \mathrm{Sin}(t * f_{1x} * 2\mathrm{pi}) + (1-n_x) * A_{2x} * \mathrm{Cos}(t * f_{2x} * 2\mathrm{pi})$; and the Y-axis offset=$n_y * A_{1y} * \mathrm{Sin}(t * f_{1y} * 2\mathrm{pi}) + (1-n_y) * A_{2y} * \mathrm{Cos}(t * f_{2y} * 2\mathrm{pi})$; wherein $n_x$ represents a variable parameter in the horizontal direction; $A_{1x}$ represents a component of the horizontal shock amplitude in the sine direction; $A_{2x}$ represents a component of the horizontal shock amplitude in the cosine direction; $f_{1x}$ represents a component of the horizontal shock frequency in the sine direction; $f_{2x}$ represents a component of the horizontal shock frequency in the cosine direction; $n_y$ represents a variable parameter in the horizontal direction; $A_{1y}$ represents a component of the vertical shock amplitude in the sine direction; $A_{2y}$ represents a component of the vertical shock amplitude in the cosine direction; $f_{1y}$ represents a component of the vertical shock frequency in the sine direction; $f_{2y}$ represents a component of the vertical shock frequency in the cosine direction; and pi represents a circumference ratio.

In step S504, a position of a first image displayed on a display unit is positioned according to the X-axis offset and the Y-axis offset. The pixel coordinates of the displayed image will be adjusted, and the adjusted pixel coordinates (Xm, Ym)=(the X+X-axis offset, the Y+Y-axis offset), wherein (X,Y) represents original pixel coordinates. That is, the position of the first imaged image displayed on the display is compensated using the calculated X-axis offset and Y-axis offset.

In step S503, based on the concept of vibration wave, the vibration-to-time relationship is converted to the vibration-to-frequency relationship.

In step S505, a first image is displayed on a display unit.

Figure 6:
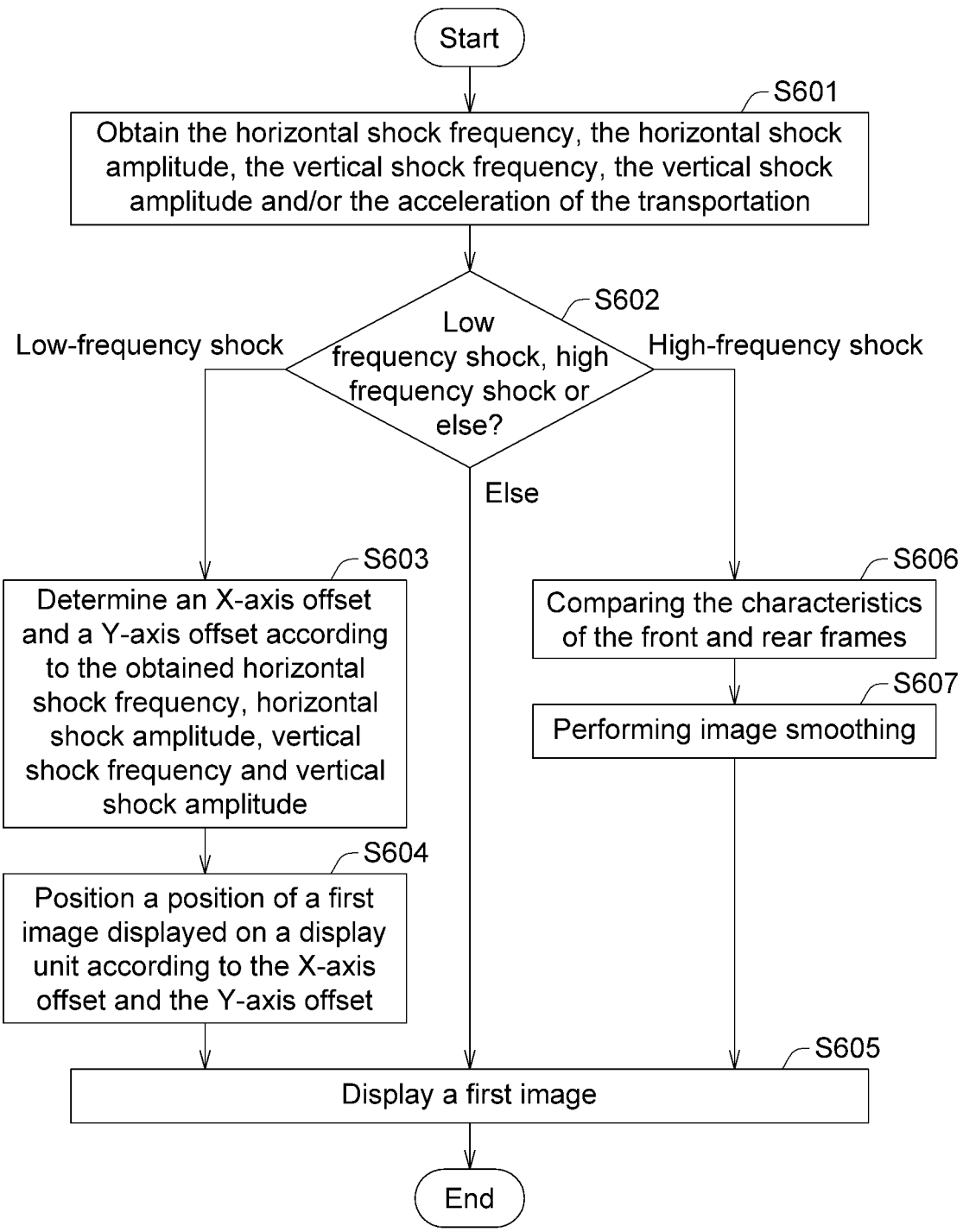
FIG. 6 is a flowchart of an image display method according to another embodiment of the present disclosure.

Referring to FIG. 6, a flowchart of an image display method according to another embodiment of the present disclosure is shown. In another embodiment, shock frequency is further divided into low-frequency shock, high-frequency shock and other shocks. The categorization is determined according to whether at least one of the obtained horizontal shock frequency, the horizontal shock amplitude, the vertical shock frequency and the vertical shock amplitude is not smaller than at least one of the corresponding first horizontal shock frequency threshold, first horizontal shock amplitude threshold, first vertical shock frequency threshold and first vertical shock amplitude threshold, wherein the first horizontal shock frequency threshold, the first horizontal shock amplitude threshold, the first vertical shock frequency threshold and the first vertical shock amplitude threshold respectively are greater than the horizontal shock frequency threshold, the horizontal shock amplitude threshold, the vertical shock frequency threshold and the vertical shock amplitude threshold. In the present embodiment, the low-frequency shock is defined as the horizontal shock frequency not smaller than horizontal shock frequency threshold but smaller than first horizontal shock frequency threshold and the vertical shock frequency not smaller than vertical shock frequency threshold but smaller than first vertical shock frequency threshold. The high-frequency shock is defined as the horizontal shock frequency not smaller than first horizontal shock frequency threshold and the vertical shock frequency not smaller than the first vertical shock frequency threshold. Based on a part of the experiment results, motion sickness is more likely to occur in the scenario of low-frequency shock and is less likely to occur in the scenario of high-frequency shock. Therefore, in the present embodiment, the image is repositioned in the scenario of low-frequency shock. In the scenario of high-frequency shock, step S606 of comparing characteristics of two subsequent images and step S607 of smoothing images are performed. In an embodiment, when the horizontal and vertical shock frequency are used in the determination, the corresponding first horizontal shock frequency threshold is 0.5 Hz, and the corresponding first vertical shock frequency threshold is 2 Hz.

In a scenario, the user is viewing mobile phone at a transportation. The processor of the mobile phone can obtain the horizontal/vertical amplitude and shock frequency through the G-sensor of the mobile phone and obtain the transportation's acceleration through the computer system of the transportation. The processor of the mobile phone can position the position of the image displayed on the display of the mobile phone according to the horizontal/vertical amplitude and shock frequency obtained through the G-sensor of the mobile phone and the transportation's acceleration obtained through the computer system of the transportation.

In another scenario, the horizontal/vertical shock detection unit can be a wearable or an embedded physiological structure. By wearing the horizontal/vertical shock detection unit, the user can more precisely measure the horizontal/vertical amplitude and shock frequency closer to that perceived through the vestibule of the user's inner ears.

Additionally, artificial intelligence may be used to optimize motion sickness compensation (the X-axis offset and the Y-axis offset). An artificial intelligence model can be created and trained using the experimental data obtained from the reading comfort experiment to predict the optimum motion sickness compensation in different shock scenarios.

Besides, the image display method of the present disclosure may be used in a head-mounted display to display the information on the head-mounted display according to the relative position between the eyes and the object. Meanwhile, if the user is in an environment with shock, the user may present motion sickness due to the difference between the motion perceived by the eyes and the motion perceived through the vestibule of the inner ears. Through the image display method of the present disclosure, after the head-mounted display calculates the position of the information or image displayed on the display according to the relative position between the eyes and the object, the position of the information or image displayed on the display can be adjusted or compensated to alleviate motion sickness.

According to the display system and the image display method disclosed in an embodiment of the present disclosure, whether motion sickness occurs is determined according to the shock and/or the acceleration received by the user at the transportation. If it is determined that motion sickness occurs, the position of the image displayed on the display is positioned according to the horizontal/vertical amplitude and shock frequency to reduce or even avoid motion sickness occurring to the user.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. An image display method for alleviating motion sickness, comprising:
   obtaining a plurality of shock and speed information of a transportation system, wherein the shock and speed information at least comprises a horizontal shock frequency or a vertical shock frequency;
   comparing the at least one of the shock and speed information comprising the horizontal shock frequency or the vertical shock frequency with one or more than one corresponding threshold to determine whether motion sickness occurs; and
   in response to the determination that motion sickness occurs, positioning a position of a first image displayed on a display unit according to the shock and speed information comprising the horizontal shock frequency or the vertical shock frequency.

2. The image display method according to claim 1, wherein the shock and speed information comprises the horizontal shock frequency, a horizontal shock amplitude, the vertical shock frequency, a vertical shock amplitude and/or an acceleration.

3. The image display method according to claim 2, wherein when positioning a position of a first image displayed on a display unit according to the shock and speed information, a X-axis offset and a Y-axis offset are determined according to the horizontal shock frequency, the horizontal shock amplitude, the vertical shock frequency and the vertical shock amplitude, and the position of the first image displayed on the display unit is positioned according to the X-axis offset and the Y-axis offset.

4. The image display method according to claim 3, wherein the X-axis offset=$n_x*A_{1x}*Sin(t*f_{1x}*2pi)+(1-n_x)*A_{2x}*Cos(t*f_{2x}*2pi)$; and the Y-axis offset=$n_y*A_{1y}*Sin(t*f_{1y}*2pi)+(1-n_y)*A_{2y}*Cos(t*f_{2y}*2pi)$; $n_x$ represents a variable parameter in the horizontal direction; $A_{1x}$ represents a component of the horizontal shock amplitude in the sine direction; $A_{2x}$ represents a component of the horizontal shock amplitude in the cosine direction; $f_{1x}$ represents a component of the horizontal shock frequency in the sine direction; $f_{2x}$ represents a component of the horizontal shock frequency in the cosine direction; $n_y$ represents a variable parameter in the horizontal direction; $A_{1y}$ represents a component of the vertical shock amplitude in the sine direction; $A_{2y}$ represents a component of the vertical shock amplitude in the cosine direction; $f_{1y}$ represents a component of the vertical shock frequency in the sine direction; $f_{2y}$ represents a component of the vertical shock frequency in the cosine direction; and pi represents a circumference ratio.

5. The image display method according to claim 1, further comprising:
   comparing the at least one of the shock and speed information with one or more than one first threshold to determine whether to perform a smoothing treatment on the first image,
   wherein the one or more than one first threshold is greater than one or more than one corresponding threshold.

6. The image display method according to claim 2, wherein it is determined that motion sickness occurs when at least one of the following conditions is met; the conditions are: the horizontal shock frequency is not smaller than 0.1 Hz, the vertical shock frequency is not smaller than 1 Hz and the absolute value of the acceleration is not smaller than 9 m/s$^2$.

7. An image display system for alleviating motion sickness, comprising:
   one or more than one detection unit;
   a display unit;
   a processing unit coupled to the one or more than one detection unit and the display unit, wherein the processing unit is configured to:
   obtain a plurality of shock and speed information of a transportation system by the one or more than one detection unit, wherein the shock and speed information at least comprises a horizontal shock frequency or a vertical shock frequency;
   compare the at least one of the shock and speed information comprising the horizontal shock frequency or the vertical shock frequency with one or more than one corresponding threshold to determine whether motion sickness occurs; and
   in response to the determination that motion sickness occurs, position a position of a first image displayed on the display unit according to the shock and speed information comprising the horizontal shock frequency or the vertical shock frequency.

8. The image display system according to claim 7, wherein the shock and speed information comprises the horizontal shock frequency, a horizontal shock amplitude, the vertical shock frequency, a vertical shock amplitude and an acceleration.

9. The image display system according to claim 8, wherein when positioning a position of a first image displayed on a display unit according to the shock and speed information, a X-axis offset and a Y-axis offset are determined according to the horizontal shock frequency, the horizontal shock amplitude, the vertical shock frequency and the vertical shock amplitude, and the position of the first image displayed on the display unit is positioned according to the X-axis offset and the Y-axis offset.

10. The image display system according to claim 9, wherein the X-axis offset=$n_x*A_{1x}*Sin(t*f_{1x}*2pi)+(1-n_x)*A_{2x}*Cos(t*f_{2x}*2pi)$; and the Y-axis offset=$n_y*A_{1y}*Sin(t*f_{1y}*2pi)+(1-n_y)*A_{2y}*Cos(t*f_{2y}*2pi)$; $n_x$ represents a variable parameter in the horizontal direction; $A_{1x}$ represents a component of the horizontal shock amplitude in the sine direction; $A_{2x}$ represents a component of the horizontal shock amplitude in the cosine direction; $f_{1x}$ represents a component of the horizontal shock frequency in the sine direction; $f_{2x}$ represents a component of the horizontal shock frequency in the cosine direction; $n_y$ represents a variable parameter in the horizontal direction; $A_{1y}$ represents a component of the vertical shock amplitude in the sine direction; $A_{2y}$ represents a component of the vertical shock amplitude in the cosine direction; $f_{1y}$ represents a component of the vertical shock frequency in the sine direction; $f_{2y}$ represents a component of the vertical shock frequency in the cosine direction; and pi represents a circumference ratio.

11. The image display system according to claim 7, further comprising:
  comparing the at least one of the shock and speed information with one or more than one first threshold to determine whether to perform a smoothing treatment on the first image,
  wherein the one or more than one first threshold is greater than one or more than one corresponding threshold.

12. The image display system according to claim 8, wherein it is determined that motion sickness occurs when at least one of the following conditions is met; the conditions are: the horizontal shock frequency is not smaller than 0.1 Hz, the vertical shock frequency is not smaller than 1 Hz and the absolute value of the acceleration is not smaller than 9 m/s$^2$.

\* \* \* \* \*